(12) United States Patent
Lingren et al.

(10) Patent No.: US 9,518,941 B1
(45) Date of Patent: Dec. 13, 2016

(54) WEIGHT-PERCENT ANALYSIS FOR PROMPT GAMMA NEUTRON ACTIVATION SUBSTANCE ANALYZERS

(71) Applicant: Sabia Inc., San Diego, CA (US)

(72) Inventors: Clinton LaMar Lingren, San Diego, CA (US); James Francis Miller, Solana Beach, CA (US); Stephen James Foster, Vista, CA (US)

(73) Assignee: Sabia Inc., San Diego, CA (US)

( * ) Notice: Subject to any disclaimer, the term of this patent is extended or adjusted under 35 U.S.C. 154(b) by 0 days.

(21) Appl. No.: 15/224,189

(22) Filed: Jul. 29, 2016

(51) Int. Cl.
*G01V 5/10* (2006.01)
*G01N 23/222* (2006.01)

(52) U.S. Cl.
CPC .................. *G01N 23/222* (2013.01)

(58) Field of Classification Search
CPC .......... B07C 5/344; B07C 5/346; C22B 1/005; G01N 23/222; Y02P 10/214
USPC ...................................................... 250/269.6
See application file for complete search history.

(56) References Cited

U.S. PATENT DOCUMENTS

| | | | |
|---|---|---|---|
| 4,171,485 A | 10/1979 | Marshall | |
| 4,582,992 A | 4/1986 | Atwell | |
| 4,694,165 A | 9/1987 | Proctor | |
| 5,959,870 A * | 9/1999 | Hurwitz | B65G 69/10 198/508 |
| 6,157,034 A | 12/2000 | Griebel | |
| 6,396,061 B1 | 5/2002 | Madden | |
| 7,152,002 B2 | 12/2006 | Lingren | |
| 7,778,783 B2 | 8/2010 | Lingren | |
| 8,426,821 B2 | 4/2013 | Harris | |
| 9,291,580 B2 | 3/2016 | Lingren | |
| 2003/0225531 A1* | 12/2003 | Lingren | G01T 3/06 702/23 |
| 2005/0004763 A1* | 1/2005 | Osucha | G01N 23/223 702/8 |

(Continued)

OTHER PUBLICATIONS

Evans, et al., "Extending the Life of Your Legacy PGNA Cement Analyzer through a 3rd Party Retrofit", Sabia Inc., Technical Papers, 2015, 7 pages.

(Continued)

*Primary Examiner* — David J Makiya
*Assistant Examiner* — Taeho Jo
(74) *Attorney, Agent, or Firm* — Fish & Richardson P.C.

(57) ABSTRACT

Methods and systems are provided to improve PGNAA substance analyzers. In one aspect, an analyzer includes: a source of neutrons; an opening to receive a substance; a gamma ray detector; and computational device(s) configured to receive spectral data of detected gamma rays, perform a regression algorithm on the spectral data using spectral responses for known atomic elements to determine coefficients of spectrum, sum effective weight values (corresponding to the coefficients of spectrum) together to form a total effective weight value for the substance being analyzed, divide effective weight values by the total effective weight value for the substance to generate effective weight-percent values corresponding to two or more respective ones of the atomic elements detected in the spectral data, and generate final weight-percent values based on a correlation of previous effective weight-percent values obtained for known samples with elemental or molecular weight-percent values obtained for the known samples.

25 Claims, 3 Drawing Sheets

(56) References Cited

U.S. PATENT DOCUMENTS

2006/0115037 A1* 6/2006 Pedersen ............... B07C 5/346
376/159

OTHER PUBLICATIONS

Sabia Inc., Technical Papers, http://sabiainc.com/about-sabia/technical-papers/ 6/27, downloaded from the Internet, Jun. 27, 2016, 4 pages.

Sowerby, et al., "On-Conveyor Belt Determination of Ash in Coal". In Hardy, C.J. (Ed.). Second International Conference on Isotopes, Conference proceedings, Australia, 1997, 7 pages.

Leetham, "Online Stockpile Analysis",: http://www.thermoscientific.com/content/dam/tfs/ATG/CAD/CAD%20Documents/Third-Party%20Papers/Cement,%20Coal,%20Minerals%20Sampling%20and%20Online%20Analysis/Cement%20Online%20Elemental%20Analyzers/D00459~.pdf, World Cement, Jan. 2008.

Leetham, "PGNAA Improves Process and Quality Control in Cement Production", http://acceleratingscience.com/mining/pgnaa-improves-process-and-quality-control-in-cement-production/, Jun. 17, 2014.

"Neutron Elemental Analysis", SODERN, http://www.sodern.com/sites/en/ref/Neutron-elemental-analysis__33.html, Jun. 20, 2014.

Registry of Radioactive Sealed Sources and Devices, http://www.nrc.gov/, No. GA-0716-D-101-S, Mar. 20, 1986.

Registry of Radioactive Sealed Sources and Devices, http://www.nrc.gov/, No. CA-305-D-103-S, Apr. 20, 1993.

Registry of Radioactive Sealed Sources and Devices, http://www.nrc.gov/, No. GA-0716-D-103-S, May 8, 2001.

Registry of Radioactive Sealed Sources and Devices, http://www.nrc.gov/, No. CA-1045-D-101-B, Oct. 10, 2007.

Registry of Radioactive Sealed Sources and Devices, http://www.nrc.gov/, No. CA-0305-D-101-S, Oct. 22, 2007.

Registry of Radioactive Sealed Sources and Devices, http://www.nrc.gov/, No. CA-0305-D-104-S, Oct. 22, 2007.

Registry of Radioactive Sealed Sources and Devices, http://www.nrc.gov/, No. CA-0305-D-105-S, Oct. 22, 2007.

"Thermo Fisher Scientific Launches New PGNAA Slurry Analyzer", http://www.mining.com/web/thermo/fisher-scientific-launches-new-pgnaa-slurry-analyzer/, Oct. 30, 2012.

Xuming et al., "Tentative Research on Technologic and Economic Analysis of Application of y-ray Analyzer and Raw Meal Quality Control System (Software) from Thermo Electron Corporation", 6# Report of Yunfu Tianshan Cement Co., Ltd., https://tools.thermofisher.com/content/sfs/brochures/D00462~.pdf, downloaded from the Internet Jul. 29, 2016, 15 pages.

Leetham et al., "Online Analyzers: Cf-252 Supply Chain Update and Risk Mitigation", IEEE-IAS/PCA 52nd Cement Industry Technical Conference, Mar. 31, 2010, https://tools.thermofisher.com/content/sfs/brochures/D00692~.pdf, 7 pages.

Anderson et al., "1+1=3: More from Your Online Coal Analyzer", May 2007, https://tools.thermofisher.com/content/sfs/brochures/D00456~.pdf, pp. 1-11.

* cited by examiner

WEIGHT-PERCENT ANALYSIS FOR PROMPT GAMMA NEUTRON ACTIVATION SUBSTANCE ANALYZERS

BACKGROUND

This specification relates to substance analyzers, and more particularly, to a bulk substance analyzer that can determine the weight percent values of compositional elements or molecules in bulk materials.

When an atom absorbs a neutron, it increases in atomic weight, but at that moment, the chemical properties of the atom do not change, thus forming a new isotope of the same element. When a neutron is absorbed, the absorbing atom emits one or more gamma rays, the number and energies of which are unique to that element. The new isotope may be unstable and seek stability by emitting one or more forms of radiation over a period of time, which may also result in the atom changing to a different element. Every radioactive isotope has a characteristic half-life as it decays to a stable state. An element that has absorbed a neutron can be identified by either the absorption gamma rays that it emits or by the decay-radiation it emits. The latter is normally referred to as neutron activation analysis and the former is often called Prompt-Gamma, Neutron Activation Analysis (PGNAA).

Commercial PGNAA analyzers were introduced during the 1970s and 1980s. PGNAA can measure material composition throughout a relatively large volume of material because neutrons penetrate matter to a great depth and the resulting prompt gamma rays are of energies high enough to permit them to escape from a substantial depth within the material. When the bulk material is bombarded with the neutron radiation, different characteristic gamma-ray energy spectra are produced from different elements in the bulk material. By processing detected signals indicative of gamma ray energies, a measurement can be made regarding the elemental content of the bulk material. Directing a PGNAA analyzer at a stream of industrial material can allow the full stream to be analyzed and an accurate assessment of the composition of bulk materials can be provided quickly, without special processing of the materials. For further details regarding PGNAA analyzer, see U.S. Pat. Nos. 7,152,002 and 7,778,783, which describe improvements for substance analyzers using Prompt Gamma Neutron Activation Analysis for identifying characteristics of a substance.

SUMMARY

This specification describes technologies relating to substance analyzers, and more particularly, to a bulk substance analyzer that can determine the weight-percent values of compositional elements or molecules in bulk materials.

One or more aspects of the subject matter described in this specification can be embodied in a PGNAA (Prompt-Gamma, Neutron-Activation Analysis) substance analyzer that includes: a source of neutrons; an opening arranged with respect to the source of neutrons to receive a substance; a gamma ray detector arranged with respect to the opening to detect gamma rays emanating at least from the substance in response to absorption of neutrons by the substance; and one or more computational devices configured to receive spectral data of the detected gamma rays, perform a regression algorithm on the spectral data using a data repository of spectral responses for known atomic elements to determine coefficients of spectrum for atomic elements detected in the spectral data, sum effective weight values, corresponding to the coefficients of spectrum, together to form a total effective weight value for the substance being analyzed, divide each of two or more of the effective weight values by the total effective weight value for the substance being analyzed to generate effective weight-percent values corresponding to two or more respective ones of the atomic elements detected in the spectral data, and generate final weight-percent values from the effective weight-percent values, for the substance being analyzed, based on a correlation of (a) previous effective weight-percent values obtained for known samples with (b) elemental or molecular weight-percent values obtained for the known samples.

These and other embodiments can optionally include one or more of the following features. The effective weight values can be the coefficients of spectrum determined by the regression algorithm. The final weight-percent values can be elemental or molecular weight-percent values for the substance being analyzed. The regression algorithm can be MLR (multiple linear regression). Further, the spectral responses for the known atomic elements can be provided in the data repository in units of counts per minute per gram.

The one or more computational devices are configured to generate the effective weight values in accordance with a determined relationship between magnitudes of elemental coefficients and weight values of elements or molecules. The one or more computational devices can be configured to generate the effective weight values by multiplying the coefficients of spectrum by respective ratios of molecular weight to atomic weight for detected elements. Other scaling of the coefficients of spectrum is also possible.

The source of neutrons can be an isotopic radioactive source, and the PGNAA substance analyzer can include: a neutron moderating material arranged with respect to the isotopic radioactive source to slow velocities of neutrons from the isotopic radioactive source; and a radiation shielding material arranged with respect to the opening and the gamma ray detector to reduce an amount of radiation escaping the substance analyzer. In some implementations, the source of neutrons is an electrically powered neutron generator.

Moreover, in some implementations, the one or more computational devices can be configured to receive spectral data of the detected gamma rays, perform a regression algorithm on the spectral data using a data repository of spectral responses for known atomic elements to determine coefficients of spectrum for atomic elements detected in the spectral data, use the coefficients of spectrum directly as effective weight values of the atomic elements detected in the spectral data, sum the effective weight values together to form a total effective weight value for the substance being analyzed, divide each of two or more of the effective weight values by the total effective weight value for the substance being analyzed to generate effective weight-percent values for the atomic elements detected in the spectral data, and generate molecular weight-percent values from the effective weight-percent values, for the substance being analyzed, based on a correlation of (a) previous effective weight-percent values obtained for known samples with (b) molecular weight-percent values obtained for the known samples.

The one or more computational devices can be configured to: receive calibration spectral data of gamma rays detected from the known samples; perform the regression algorithm on the calibration spectral data using the data repository of spectral responses for known atomic elements to determine calibration coefficients of spectrum for atomic elements detected in the calibration spectral data; potentially, use the calibration coefficients of spectrum directly as calibration effective weight values of the atomic elements detected in the spectral data; sum calibration effective weight values together to form a total calibration effective weight value for each of the known samples; divide each of two or more of the calibration effective weight values by the total calibration effective weight value for each respective known sample to generate the previous effective weight-percent values for the known samples; and correlate the previous effective weight-percent values with elemental or molecular weight-percent values obtained for the known samples to generate calibration data; wherein generating the final weight-percent values (e.g., the molecular weight-percent values) includes applying the calibration data to the effective weight-percent values for the substance being analyzed.

According to another aspect, a non-transitory machine readable medium encodes instructions operable to receive PGNAA spectral data and to cause a computer to perform operations including: running a regression algorithm (e.g., MLR) on the PGNAA spectral data using a data repository of spectral responses for known atomic elements to determine coefficients of spectrum for atomic elements detected in the PGNAA spectral data; summing effective weight values, corresponding to the coefficients of spectrum (e.g., the coefficients themselves or modified versions of the coefficients), together to form a total effective weight value for the substance being analyzed; dividing each of two or more of the effective weight values by the total effective weight value for the substance being analyzed to generate effective weight-percent values corresponding to two or more respective ones of the atomic elements detected in the PGNAA spectral data (e.g., effective weight-percent values for the atomic elements detected in the PGNAA spectral data); and generating final weight-percent values (e.g., molecular weight-percent values) from the effective weight-percent values, for the substance being analyzed, in accordance with calibration data generated by correlating effective weight-percent values obtained for known samples with elemental or molecular weight-percent values obtained previously for the known samples.

As noted above, the spectral responses for the known atomic elements can be provided in the data repository in units of counts per minute per gram. The operations can include generating the effective weight values in accordance with a determined relationship between magnitudes of elemental coefficients and weight values of elements or molecules. For example, the coefficients of spectrum can be multiplied by respective ratios of molecular weight to atomic weight for detected elements.

In addition, the operations can include: receiving calibration spectral data of gamma rays detected from the known samples; running the regression algorithm on the calibration spectral data using the data repository of spectral responses for known atomic elements to determine calibration coefficients of spectrum for atomic elements detected in the calibration spectral data; summing calibration effective weight values, corresponding to the calibration coefficients of spectrum (e.g., the calibration coefficients themselves or modified versions thereof), together to form a total calibration effective weight value for each of the known samples; dividing each of two or more of the calibration effective weight values by the total calibration effective weight value for each respective known sample to generate the effective weight-percent values obtained for the known samples; and correlating the effective weight-percent values obtained for the known samples with the elemental or molecular weight-percent values obtained for the known samples to generate the calibration data.

Particular embodiments of the subject matter described in this specification can be implemented to realize one or more of the following advantages. The true weight percent of elements and their associated molecules (e.g., oxides) in a substance being analyzed can be determined. This can be accomplished without requiring frequent re-calibrations and/or placement of restrictions on configurations of the presentation of the substance to the analyzer. Thus, accurate analyses can be obtained in less than ideal conditions, which conditions are common in the normal operation of PGNAA substance analyzers.

The mass flow and effective mass loading of the substances passing through a PGNAA substance analyzer need not be carefully held as close to a predefined constant as possible. Accurate PGNAA analysis can be achieved without the use of complex calibration processes or assumptions concerning a constant neutron flux profile. Errors deriving from variations in moisture content of a substance being analyzed, neutron source strength, and/or changes in macroscopic cross section of the substance (composition) can be reduced or even eliminated.

The details of one or more embodiments of the subject matter described in this specification are set forth in the accompanying drawings and the description below. Other features, aspects, and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1A:
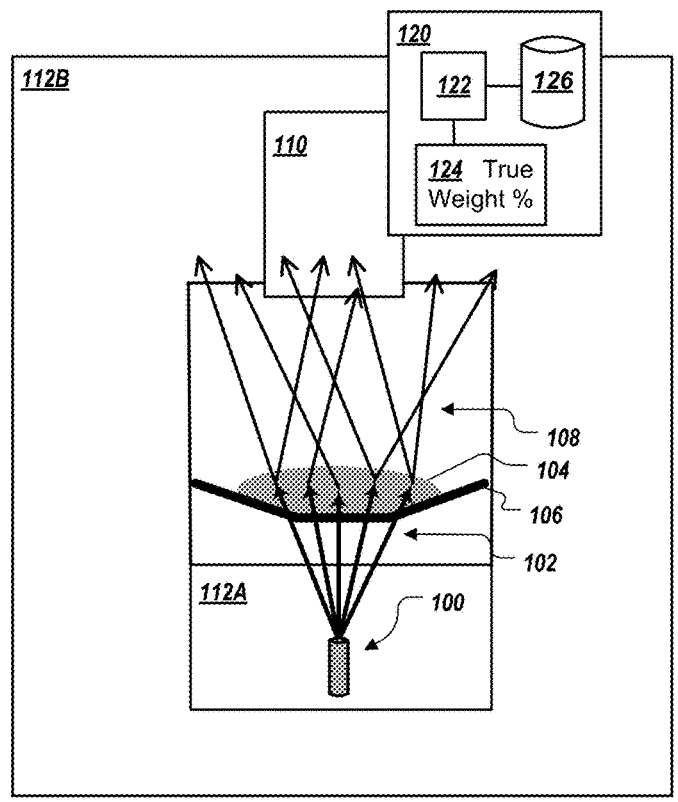
FIG. 1A shows an example of a PGNAA substance analyzer.

FIG. 1A shows an example of a Prompt-Gamma, Neutron Activation Analysis (PGNAA) substance analyzer. One or more neutron sources 100 provide neutrons 102 to impact a substance 104 to be analyzed, which can be carried on a conveyor belt 106 through a channel or opening (as shown) in the PGNAA substance analyzer. Although this description focuses on the use of conveyor belt 106, for ease of understanding, it will be appreciated that many different analyzer structures and configurations are possible, including use of a slurry pipe, a sample stream, or sample containers (e.g., automated off-line sampling systems, whether for single samples or otherwise) to deliver the substance 104 (e.g., coal or other minerals) to a location proximate to the source of neutrons 100. For further details regarding PGNAA structures and configurations that can be used, see U.S. Pat. No. 7,152,002, issued Dec. 19, 2006, U.S. Pat. No. 7,778,783, issued Aug. 17, 2010, and U.S. Pat. No. 9,291,580, issued Mar. 22, 2016, each of which is hereby incorporated by reference.

The neutron source 100 can be one or more neutron sources, e.g., one or more isotopic neutron sources and/or one or more electric neutron sources. An electric neutron source can include an electrically powered neutron generator. Typical electronic neutron generators emit neutrons by means of compact linear accelerators, which typically produce neutrons by fusing isotopes of hydrogen together. The energies of the neutrons can range from about 2.4 MeV to 14 MeV depending on which hydrogen isotopes are used. The emission of neutrons is terminated by removing the source of electric power from the generator. An isotopic neutron source can include a radioactive material (e.g., Californium-252) that emits neutrons 102, and containing material 112A is placed around the radioactive material to condition (and potentially focus) emitted neutrons 102 to bombard the substance 104.

Regardless of the specifics of the neutron source(s) 100, when the neutrons 102 impact the substance 104 to be analyzed, prompt gamma-rays 108 are generated. One or more gamma-ray detectors 110 are mounted in a location near the substance 104 (e.g., on an opposite side of the substance 104 from the neutron source 100) to detect the gamma-rays 108 and process the signals thus generated. A detector 110 can include at least one crystal (or other scintillator) and PMT (Photomultiplier) (or other photosensor) along with other components (e.g., an excitation voltage source and an amplifier). In addition, in some embodiments, the detector 110 includes integrated detector electronics and/or computational devices, such as described in U.S. Pat. No. 9,291,580, or other gamma-ray detection technology. In general, regardless of placement and/or distribution of the computational devices and electronics within the system, a computer 120 is included to process data to determine which elements absorbed the neutrons and emitted the detected prompt gamma rays. In some implementations, the computer 120 is integrated (at least partially) into the PGNAA substance analyzer unit located near the substance being analyzed. In some implementations, the computer 120 is located remotely from the PGNAA substance analyzer unit itself.

In addition, one or more materials 112B can be arranged in proximity to the neutron source 100, the substance 104, and the detector 110 to reduce an amount of radiation that can escape the PGNAA substance analyzer. In some implementations, the one or more materials 112B include the containing material(s) 112A. Many different combinations of materials 112A, 112B can be used in different structural configurations, depending on the needs of a particular PGNAA substance analyzer. Typically, there will be at least one neutron moderating material 112A arranged to slow velocities of neutrons from the neutron source 100, and also at least one radiation shielding material 112B arranged to reduce or eliminate the escape of nuclear radiation from the substance analyzer. Other materials can also be used, such as neutron and/or gamma ray reflecting material(s).

The moderating/reflecting/shielding materials 112A, 112B can include materials that contain hydrogen, oxygen, and carbon, such as polyethylene, and carbon, bismuth, lead, iron, boron, and/or wax. In some implementations, the moderating/reflecting/shielding materials 112A, 112B shield neutron-source gamma rays and moderate the energy of the neutrons in the analyzer to increase absorption of the neutrons by the atoms in the substance 104. The moderating/reflecting/shielding materials 112A, 112B can also reduce unwanted radiation in the detector and act to reflect neutrons back toward the substance 104, thereby lowering the number of neutrons that escape the analyzer. By fulfilling these functions, the moderating/reflecting/shielding materials 112A, 112B control the thermal neutron population in the PGNAA substance analyzer, and thereby enhance neutron absorption in the substance 104 while aiding neutron and gamma radiation shielding to protect personnel that may approach or work around the analyzer. In many implementations, the neutron source(s) 100 and detector(s) 110 are placed on opposite sides of the substance 104 to be analyzed and are surrounded by moderating and shielding materials 112A, 112B included in the structure of the analyzer, as shown. However, other configurations are also possible.

As an aid to understanding the present disclosure, some nuclear physics principles are described in this application in a simplified form. These descriptions are not intended to be comprehensive nor completely theoretically accurate. Rather, they are presented solely to help in understanding the benefits of the present invention as compared to prior art methods.

A neutron can exist separate from the nucleus of an atom but has a relatively short life on the order of minutes. Free neutrons are typically born with high kinetic energies in the million-electron-Volt (MeV) range and lose energy through elastic or inelastic interactions with nuclei of atoms in the medium through which they move until they are at the thermal energy of those atoms, about 0.025 eV. Most elements have a much higher probability of absorbing a thermal neutron and then promptly emit unique spectra of gamma rays. Thus, each atom of the substance 104 that absorbs a thermal neutron 102 promptly emits an array of gamma ray energies that is the unique fingerprint of that element. Note that a gamma ray is a high-energy photon of extremely high-frequency electromagnetic radiation (with energies greater than 100 keV, frequencies greater than $10^{19}$ Hertz, and wavelengths less than 10 picometers) typically emitted from the nucleus of an atom. Directional characteristics of gamma rays are somewhat similar to light emitted from a light source but without much reflection capability.

Within a PGNAA substance analyzer, neutron scattering causes the directions of neutrons 102 to continuously change so that they fill the area that they occupy in a manner similar to the way a gas fills a container into which it may be placed. Gas pressure in a closed container is uniform throughout the volume, but the neutron flux contour over its volume is not uniform. However, as gas pressure increases or decreases uniformly by addition or deletion of gas molecules independent of the location of the exchange, even so, the magnitude of the neutron flux contour decreases throughout its area as neutrons are removed by an absorber at any place in the area, or increases by elimination of such an absorber from any location within that area. Likewise, a change in the intensity of a neutron source 100 changes the magnitude of the neutron flux at all locations proportionally.

An element's microscopic neutron absorption cross section is the probability of an atom of that element absorbing a neutron and has dimensions of area in barns ($10^{-24}$ cm$^2$). The idea is that an element with a cross section of one barn provides a target as big as the broad side of a barn, so to speak. Each atom has a unique microscopic cross section, which is the probability of its absorbing a neutron in a uniform neutron flux.

The macroscopic neutron absorption cross section is the probability of all of the atoms of an element in a one-cubic-centimeter of the material absorbing neutrons. It is obtained by multiplying the microscopic cross section times the atom density of that element in the volume of the material and has the dimension of cm$^{-1}$ (cm$^2$ times cm$^{-3}$). The sum of all of the macroscopic cross sections of all of the elements in a material gives the macroscopic cross section of that material for absorbing neutrons 102.

In addition, gamma ray attenuation should be considered. Gamma rays 108 of interest in PGNAA applications generally fall in the range of 1 MeV to 10 MeV and interact with materials by three major processes: photoelectric absorption, Compton scattering, and pair production. In the photoelectric absorption process, the gamma ray loses all of its energy in one interaction. The probability for this process depends strongly on gamma-ray energy E and atomic number Z. In Compton scattering, the gamma ray loses only part of its energy in one interaction. The probability for this process is weakly dependent on E and Z. The gamma ray can lose all of its energy in one pair-production interaction. For PGNAA applications it is important to note that gamma ray attenuation is different for every substance 104, depending on its specific composition, and the objective is to get the gamma rays into the detector (e.g., into the crystal for the purpose of creating photons as a result of scintillation). Further, within any single substance 104, gamma ray attenuation is different for every gamma-ray energy. Therefore, the gamma ray attenuation is strongly affected by the composition of the substance 104 being analyzed and by the thickness of the substance 104 through which the gamma rays must pass before entering a detector 110.

Finally, neutron flux is the number of neutrons per second that pass through an area of one square centimeter ($n\text{-}cm^{-2}\text{-}sec^{-1}$). The neutron flux times the macroscopic cross section of a substance 104 is the number of neutrons 102 per second that are absorbed in one cubic centimeter of a substance 104. As a neutron flux passes through a substance 104, it is depleted by the absorption of neutrons and, therefore, becomes exponentially smaller with distance through the substance 104.

With this understanding of the nuclear physics principles involved, the operation of the PGNAA substance analyzer of FIG. 1A is now described in further detail. The computer 120 includes at least one processor 122, e.g., a central processing unit (CPU), a microprocessor, a coprocessor, multiple processor cores, etc. The computer 120 also includes at least one non-transitory machine readable medium 124, which can include both volatile memory and nonvolatile memory. The non-transitory machine readable medium can be a machine-readable storage device (e.g., a hard disk drive), a machine-readable storage substrate (e.g., an optical disc), a memory device (e.g., solid state memory, such as flash RAM (Random Access Memory), DRAM (Dynamic Random Access Memory), or SRAM (Static Random Access Memory)), or a combination of one or more of them. The non-transitory machine readable medium encodes instructions operable to cause the processor(s) 122 to obtain PGNAA spectral data from the detector(s) 110 and generate true weight percent values for the substance 104 being analyzed. In some implementations, this includes the use of a data repository 126, which can be included in the non-transitory machine readable medium 124 that holds the instructions or in another non-transitory machine readable medium, where the data repository 126 stores spectral response data for known atomic elements, generated calibration data, and potentially elemental or molecular weight-percent values obtained from known samples (e.g., that are similar to the substance 104 to be analyzed). The data repository 126 can be a database, a flat file, a spreadsheet document, etc.

PGNAA is uniquely suited for analyzing bulk non-homogeneous materials because neutrons 102 can pass completely through the substance 104 and gamma rays 108 born deep within the substance 104 have sufficient energy to pass through the substance 104 to the detector 110. The purpose of the analysis is to determine the total weight percent of each element or compound that makes up the substance 104. PGNAA does not measure compounds directly, but only elements. However, elements in a material are often associated with only one compound or a limited number of compounds. In those cases the amount of a compound or ultimate molecular combination appropriate to the application can be determined from the elemental analysis.

Fast and epithermal neutrons 102 are emitted from the source 100, are moderated to thermal energy and are absorbed in the substance 104 being analyzed (the signal) and also in the shielding and structural materials 112A, 112B in the analyzer (the background). Prompt gamma rays are emitted by all atoms that absorb neutrons. The detector 110 converts the gamma rays to electronic pulses that are processed by the electronics and computer 120 to provide the substance analysis. Major emphasis is placed on maximizing the signal counts and minimizing the background counts. The count rate of the signal from each element can be associated with the total number of atoms of that element in the material being analyzed and, therefore, the total weight of that element or the associated compound. To determine the true weight percent of an element or associated compound, the ratio of the weight of the element or associated compound to the weight of the substance 104 should be determined.

The determination of the counts associated with an element is straight forward and quite precise, but relating those counts to the mass of that element is subject to error because of changing conditions in the substance 104 (e.g., as the conveyor belt 106 moves an ever changing amount and composition of the substance 104 through the analyzer). Determining the associated total effective mass of the substance 104 being analyzed (the sample) is also very difficult and the cause of error encountered with prior PGNAA analyzers. The relationship between the counts associated with an element and the weight percent of that element in substance 104 changes as the neutron flux profile changes, as the substance 104 mass or depth changes, and/or as the macroscopic neutron absorption cross section of the substance 104 changes. In many prior art analyzers, the calibration is based on the implicit assumption that the mass and volume of the substance 104 is constant. In contrast, the PGNAA substance analyzer of FIG. 1A is able to significantly reduce or eliminate errors caused by the changes noted above.

Figure 1B:
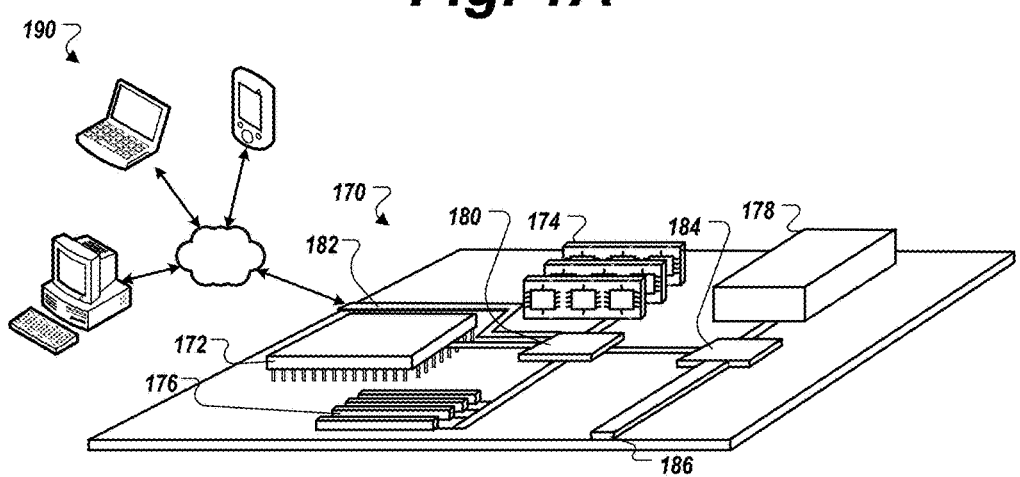
FIG. 1B shows an example of a computer architecture and associated computing devices that can be used with the PGNAA substance analyzer of FIG. 1A.

FIG. 1B shows an example of a computer architecture and associated computing devices that can be used with the PGNAA substance analyzer of FIG. 1A. A computing device 170 is a digital computer that includes a hardware processor 172, memory 174, a bus interface 180 (e.g., a parallel or serial interface), and an input/output (I/O) interface 182. One or more computing devices 170 can be included in the detector(s) 110, the computer(s) 120, or both. In some implementations, electronics are integrated into the detector(s) 110, where the electronics are configured to receive and process analog signals and output digital detection signals. Thus, the computing device 170 can include an ADC (analog to digital converter) and DAC (digital to analog converter) chip.

The memory 174 can include volatile memory, non-volatile memory, or both. For example, the memory 174 can hold firmware instructions that are run by the hardware processor 172 to perform the functions of the electronics in the detector(s) 110. In some implementations, the bus interface 180 is a high-speed interface, and the computing device 170 can include a low speed bus interface 184 to connect with a storage device 178 (e.g., a hard disk drive or solid state memory device). The storage device 178 can include software that is loaded into memory 174 and is run by the hardware processor 172 to perform the functions of the electronics. As will be appreciated, the memory 174 and the storage device 178 are examples of a computer-readable medium. Moreover, in some implementations, the computing device 170 can include one or more high-speed expansion ports 176 and one or more low-speed expansion ports 186.

In some implementations, the electronics in the detector(s) 110 can be used for controlling the detector(s) 110 and for receiving and processing the signals from the detector(s) 110 and providing communications to systems that may use the analyzer outputs. The electronics can also control the excitation of the detector and condition the signal from the detector. The electronics can include circuitry and computer hardware and software for controlling the detector and conditioning and processing the signal to extract the desired information about the substance being analyzed and for communicating that information to another device (e.g., a device on a network) where it can be further processed and formatted to satisfy the needs of the particular application.

One or more of additional computing devices 190 (e.g., a desktop computer, a laptop computer, a smartphone) can be used for display and monitoring, administrative control, additional signal analysis, or a combination of these. The additional computing device(s) 190 can be connected to the computing device 170 via a network, as shown, which can be a private local area network, a public internetwork, a virtual private network, etc. In some implementations, initial signal processing is performed by a computer within a detector, and further signal processing and analysis is performed by a separate computer to which digital signal data is communicated. In other implementations, a single computer does all the signal processing and analysis described herein. In any case, the computer 120 from FIG. 1A is representative of all such implementations, and so the computer 120 represents the computing device 170, the additional computing device(s) 190, or a combination of these, including implementations where some or all of the analysis processing is performed within a detector 110.

The neutron flux entering the substance 104 is comprised of thermal, epithermal, and fast neutrons. Essentially only thermal neutrons are absorbed in the substance 104. Fast and epithermal neutrons are scattered and slowed in the substance 104 and may become thermal neutrons and be absorbed, and the remainder escape from the substance 104 and are lost or may be scattered back into the substance 104 by moderating, shielding, and structural materials 112A, 112B.

The percent of gamma rays 108 emitted from an atom in the substance 104 that arrive at the detector 110 is determined by the position of the atom with respect to the detector 110 and their transmission through the materials between that atom and the detector. The intensity of gamma radiation 108 at the detector 110 is approximately inversely proportional to the square of the distance from its point of origin to the sensing point in the detector 110. In addition, the gamma radiation 108 is attenuated by the material of the substance 104 through which the gamma radiation 108 passes.

The total number of neutrons 102 that are absorbed in the substance 104 is a function of the neutron flux level, the moderating ratio in the substance 104, the amount of material in the substance 104, and the macroscopic cross section of the substance 104. Moisture level in the substance 104 has a major effect on the moderating ratio because hydrogen is the element that is the most effective in moderating neutrons. A higher moisture level allows a higher percent of neutrons to be thermalized and, therefore, the absorption of more neutrons in the substance 104 results. More moisture also moves the vertical position where the percent thermal neutrons is greatest to a lower position in the substance 104. More material in the substance 104 (e.g., greater bed depth on the belt 106) increases the number of atoms that can absorb neutrons but diminishes the signal from the lower atoms because of increased attenuation in the substance 104.

The macroscopic cross section of the substance 104 also affects the number of neutrons 102 absorbed in the substance 104. The macroscopic cross section of the substance 104 is the sum of the macroscopic cross sections of all of the elements in the substance 104. The macroscopic cross section of each element is different. Therefore, the macroscopic cross section of the substance 104 changes as its composition changes and the neutron absorption rate in the substance 104 changes accordingly.

All of these factors affect the calibration of an analyzer and should be taken into account. The weight percent of an element in the substance 104 is evaluated from the total count-rate of the spectrum for that element, but the count-rate per gram of the element changes continuously because of all of the above factors. In addition, the effective mass of the substance 104 and the effective mass of each element in the substance 104 should be determined in order to determine the weight-percent of each element, but prior approaches to determining the effective mass of the substance 104 are typically not as accurate as may be desired.

One approach to determining the weight (and thus the mass) of the substance 104 is to use a belt scale. But the output of a belt scale includes both the weight of the substance 104 and the weight of the belt. To address this issue, an offset can be used to subtract the weight of the belt. This method can be relatively accurate in measuring the physical weight of the substance 104 but does not fully solve the problem. The number of gamma rays 108 arriving at the detector 110 can be related to the actual mass of the sample for one set of conditions, but, as macroscopic cross section of the substance 104 or the moderating ratio in the substance 104 or the depth of the substance 104, or the average thermal neutron flux level in the substance 104 change, the ratio of counts to mass also changes.

Another approach used with PGNAA is to determine the weight-percent composition of a sample without actually determining the total weight of the sample. Elements in the substance 104 are identified using multiple linear regression (MLR), which is a statistical technique that analyzes the relationship between two or more variables and uses the information to estimate the value of the dependent variables. A library of the spectral responses for the elements of interest is used by the MLR analysis to determine the amounts of the elemental response spectra that, when added together, match the acquired spectrum of the substance 104 being analyzed. The output of an MLR calculation is a set of coefficients that when multiplied times the elemental response spectra enable matching their sum to the acquired spectrum. These coefficients are then correlated to the composition of elements or compounds, such as oxides, in the sample material.

Mathematical statistical techniques, such as provided by Solver in the EXCEL® program, available from Microsoft of Redmond, Wash., or Matlab, available from MathWorks of Natick, Mass., are applied to relate these coefficients to known weight-percent values for each element or oxide.

Using this method, from three to thirty different samples of material for which the composition is known are measured with the analyzer. Solver or another mathematical analysis program is then used to derive an equation for each element to correlate its coefficient to the known composition in each of the known samples. These relationships that are established with known materials constitute the calibration data and are used to determine the values for an unknown material that is analyzed.

This technique can directly calibrate a PGNAA analyzer for measuring oxides or other compounds for which a unique relationship to the measured elements can be established or the technique can calibrate the PGNAA analyzer measuring the weight percent of each element in the sample. However, the calibration is strictly valid only for the set of operational conditions with which the known samples were measured, i.e., the same mass, the same range of compositions, the same neutron flux level, etc. In practice, the same set of operational conditions for a PGNAA analyzer can rarely (if ever) be fully maintained.

Note that the set of operational conditions includes the mass flow of the substance 104 through the PGNAA analyzer. Thus, accurate analysis is dependent upon maintaining a constant mass flow with the same effective mass loading as was used with the prior known samples during calibration of the PGNAA analyzer or as adjusted at installation. Erratic mass flow conditions, or even uniform mass flow conditions at flow levels other than what was used during calibration, will degrade the accuracy of the PGNAA analyzer. This happens for several reasons.

A typical spectrum obtained for a substance 104 on a conveyor belt 106 may have about 5% of its total counts in the energy range from 2.5 MeV to 9.0 MeV that is used for the analysis. The majority of the counts are of lower energy and are from the substance 104 and from the analyzer structure and shielding materials 112A, 112B. When the mass of the substance 104 is increased, more neutrons 102 are absorbed in the substance 104, leaving fewer neutrons for generating background counts. Although the counts from the gamma rays 108 from the substance 104 increase, the total counts in the spectrum may actually decrease. When the mass of the substance 104 is less than what was used in the calibration, the reverse is true. If the mass of a substance 104 in an analyzer is changed, the analyzer will provide a different analysis; the magnitude of the difference is error, and its magnitude depends on the magnitude of the change in mass and the specifics of the calibration.

The spectral counts in the primary analysis range of the spectrum include both sample counts and background counts. Background counts from below the substance 104 are not affected as much by the number of neutrons 102 absorbed in the substance 104 but are affected by attenuation through the substance 104. Since the neutron source 100 is also below the substance 104, the neutron flux level is highest in this region, and any elements in this area that emit gamma-ray energies will also become part of the analysis. As the mass of the substance 104 changes, the attenuation of gamma rays that pass through the substance 104 to the detector will also change and be interpreted as an apparent change in the composition of the substance 104.

Note that a calibration done with a typical prior art method is based on an assumption that the neutron flux profile through the substance 104 remains constant and implicitly assumes that the mass and composition of the substance 104 remain constant. However, a change in composition of the substance 104 changes the macroscopic cross section of the substance 104 and thereby changes the neutron flux profile. A change in the intensity of the neutron source 100 will also change the magnitude of the entire spectrum and will accordingly change the analysis from the analyzer. For this reason, traditional analyzers need new calibrations as an isotopic neutron source decays or if the macroscopic neutron absorption cross section of the substance 104 changes significantly.

Since the rate of decay of an isotopic source is fixed by nature, it can be partially compensated by an exponential decay curve compensation. However, such compensation is not complete because the actual number of counts has changed with resulting changes in precision, etc. Neutron generators maintain a constant neutron emission rate that is controlled by electronic circuitry, but there are a number of failure mechanisms that must be considered, and the magnitude of the neutron emission may not be as precise as knowledge of the neutron emission from an isotopic source.

Moreover, as the moisture content in the substance 104 changes, the mass of the substance 104 also changes without changing the amount of each of the other elements in the sample. Likewise, since water is a very efficient moderator of neutrons, the magnitude and profile of thermal neutrons in the sample may also change with changes in moisture content. These changes are sources of error in prior art analyzers.

Finally, a background spectrum can be obtained without a sample in the analyzer, i.e., with the conveyor 106 empty. This spectrum can be subtracted by MLR or otherwise from a spectrum taken with the substance 104 inserted to attempt to get a resulting spectrum of just the sample. However, the background spectrum will have more total counts than the substance-plus-background spectrum, and its shape will be different. The reason that the composite spectrum has a lower count rate than the background spectrum is that the neutrons absorbed in the substance 104 are no longer available to be absorbed in the shielding and structure 112A, 112B of the analyzer. A major reason that the shape is different is that the neutron flux level in the materials below the substance 104, although reduced, will be reduced less than in other areas of the PGNAA substance analyzer, and the gamma rays emitted from below the substance 104 will be attenuated by the substance 104. That effect also changes with changes in the mass of the substance 104. Therefore, efforts to subtract background counts often introduce additional error.

To improve the operations of a PGNAA substance analyzer, a normalization process can be employed to effectively account for variation from sample to sample, and in particular, for variation in the total weight of a given sample. For example, if the spectral responses are normalized to the same total counts, the output of MLR can be treated as a number proportional to mass. Moreover, the mass of any given element can be expressed in a ratio form, with the sum of all the masses in the denominator, thus creating a weight percent value.

Figure 2A:
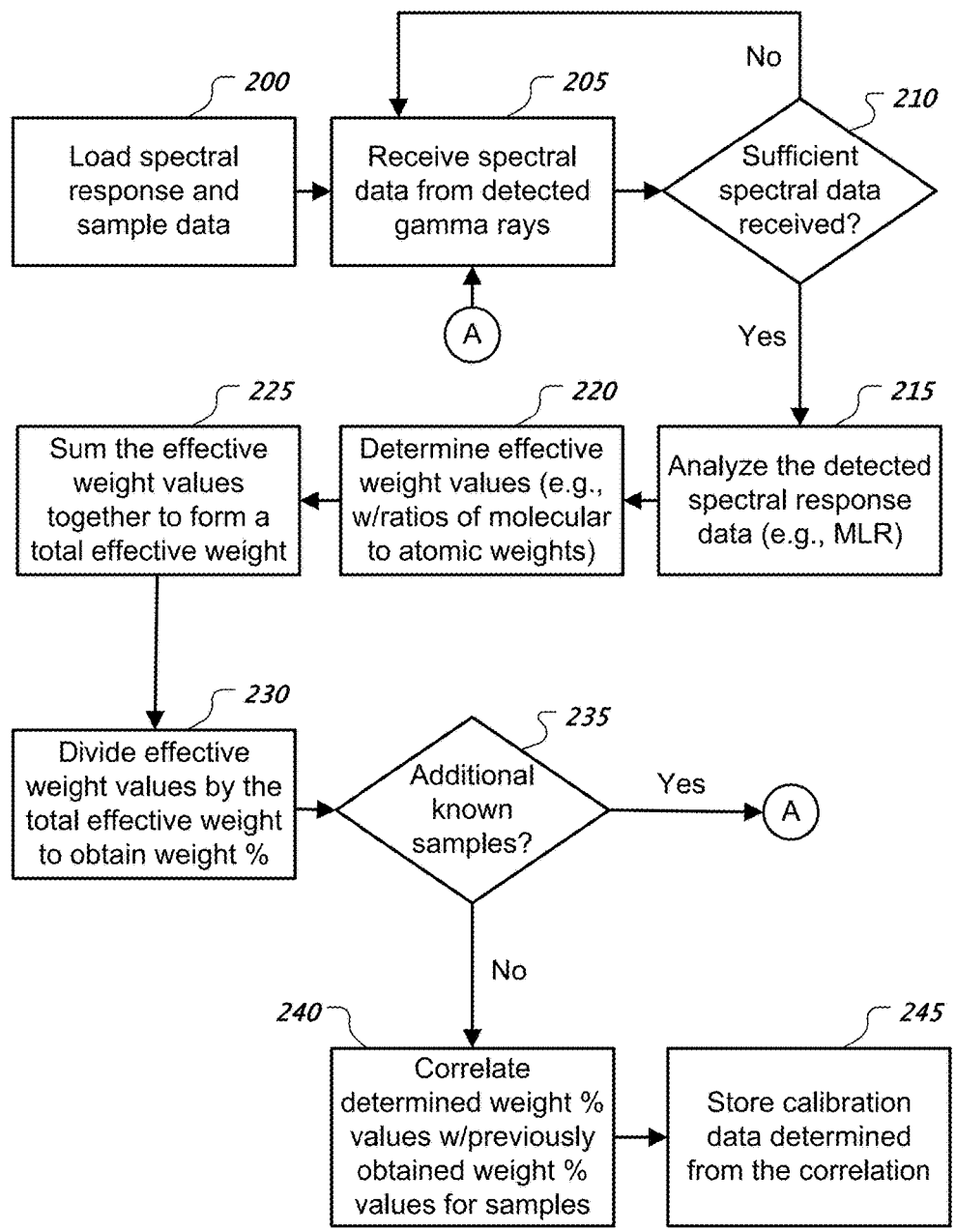
FIG. 2A shows an example of a process of calibrating a PGNAA substance analyzer to generate true weight percent values.

FIG. 2A shows an example of a process of calibrating a PGNAA substance analyzer to generate true weight percent values. Spectral response data for known atomic elements are loaded 200, e.g., loaded by computer 120 from data repository 126. These spectral responses are data obtained from observations of gamma rays emitted by individual atomic elements, e.g., under laboratory conditions, and saved in the data repository 126. These spectra can be similar to (or be) what is found in text books, but are typically determined by independent analysis using a specific detector since the spectra can be unique to the detector being used. In some implementations, the entire spectrum of gamma rays of an element that is emitted promptly when that element absorbs a neutron can be used. In other implementations, only a portion of the entire spectrum is used. Moreover, in some implementations, the spectral responses for the known atomic elements are provided in the data repository in units of counts per minute per gram to facilitate processing of the data.

In addition, elemental weight-percent values and/or molecular weight-percent values obtained from known samples are loaded 200, e.g., loaded by computer 120 from data repository 126. In other implementations, this sample data is loaded later in the process. In some implementations, five known samples are used to calibrate the PGNAA substance analyzer, and these five known samples are placed in the analyzer in turn. In other implementations, more or fewer known samples are used, depending on the needs of the particular application.

In addition, the known samples can be samples of the type of substance 104 that will be analyzed. For example, for calibration using samples from a particular site, five samples can be assembled in such a way that the samples cover the entire range of quality for each of the elements and/or compounds (e.g., oxides) of interest, and such that the range of qualities are dispersed as evenly as possible between the extremes. In addition, the samples should contain moisture content that is typical for the particular site's operations. Moreover, the known samples can be obtained by combining pure substances in a matrix that is appropriate for the application or by getting samples of material from the application and having them analyzed in a laboratory.

With the respective known samples present in the analyzer, the PGNAA substance analyzer receives 205 spectral data from the known samples to generate calibration data for the PGNAA substance analyzer. In some implementations, the process waits 205 for spectral data from detected gamma rays, and continuously, regularly or upon user input, checks 210 whether sufficient detected spectral data has been received. In some implementations, the process waits 205 for a predefined period of time and/or until a sufficient number of counts are received before determining 210 that sufficient spectral data is available for further processing. For example, in some implementations, counts data is collected every five seconds, and the five second count data can be accumulated over a longer period of time, e.g., one hour, to create a data set that is ready to analyze. Other time amounts can be used, provided sufficient counts of gamma ray detections are received, e.g., upwards of ten million counts for a response spectrum to be analyzed.

Once sufficient spectral data for a known sample has been received, the detected spectral response data is analyzed 215. This can involve performing a regression algorithm on the detected spectral data using the loaded spectral responses for known atomic elements to determine coefficients of spectrum for atomic elements detected in the spectral data. For example, MLR (multiple linear regression) can be used to determine the amount of each element's characteristic spectrum that is needed to duplicate the acquired spectrum of the current known sample. Other regression algorithms that can be used in various implementations include logistic regression, polynomial regression, stepwise regression, ridge regression, Lasso regression, and elastic net regression. Note that MLR tends to filter out the background signal during the processing, so some implementations process the full signal from the PGNAA detector(s). In other implementations, an initial background signal subtraction can be used to pre-process the detection data before the analysis 215. In many implementations, accounting for background effects is accomplished by including a separate response for the background to ensure that the meaningful elemental information is not misallocated to other spectra.

The analysis 215 (e.g., MLR) can proceed in a discretized fashion, where the spectrum is measured in counts per energy bucket of the gamma-ray energy. For example, the gamma ray count data can be analyzed in 512 channels, such that MLR will solve one equation per channel. Other numbers of channels for the spectrum data can also be used in other implementations. In any case, matrix algebra can be used to match the spectral response data detected for the known sample with the spectral response data for known atomic elements, thereby generating a coefficient for each atomic element.

If an elemental reference spectrum (the acquired spectrum of the elements) is close to perfect, the coefficient of that spectrum (determined by MLR or another technique) times the counts in each channel of the reference spectrum yields a spectrum that is contributed by that element to the detected spectral response. The coefficients can be directly correlated to the masses of the elements. Effective weight values are determined 220 based on the calculated coefficients. In some implementations, the determined coefficients of spectrum themselves are used as the effective weight values. Note that these are "effective" weight values because they correlate with the real weights but are not the real weights themselves. In other implementations, the effective weight values are generated using the calculated coefficients of spectrum as input.

For example, the effective weight values can be generated in accordance with a determined relationship between magnitudes of elemental coefficients and weight values of elements or molecules expected to be found in the known sample. In the case of elemental weight values, the determined relationship accounts for known isotopic variation in the elements typically found at a given location (e.g., based on samples from a site for which the PGNAA analysis will be performed). In the case of molecular weight values, the determined relationship accounts for the additional weight provided by known molecular compounds typically found at a given location. If the weight of an element is determined, it can be correlated to the mass of an oxide or other molecule by multiplying times the ratio of the molecular weight of that molecule to the atomic weight of that element, as described in further detail below. Other modifications of the calculated coefficients of spectrum can also be performed at 220 to arrive at effective weights for use in the subsequent processing.

As noted, in some implementations, the effective weight values of molecules are generated 220 from the coefficients of spectrum in accordance with a determined relationship between magnitudes of elemental coefficients and weight values of molecules expected to be found in the sample (e.g., correlated to the masses of the oxides). A common application of PGNAA is measuring the weight percent of oxides in bulk materials. In such applications, as described herein, the total mass of the material is the sum of the masses of the various compounds in the material:

$$W_{(total)} = \Sigma(W_{(O(i))}) \quad (1)$$

where i=1 . . . n for the oxides of elements H, B, etc. that are in the material. Since PGNAA essentially does not measure oxygen, the oxides are determined by multiplying the weight of the elements that can be measured by the ratio of the molecular weights of the oxides to the atomic weights of the elements:

$$W_{O(i)} = W_{E(i)}(M_{(O(i))}/A_{(E(i))}) \quad (2)$$

where W is the weight of the oxide or element, M is the molecular weight of the oxide, and A is the atomic weight of the element. Each oxide in the material should be included. For example, $H_2O$ is the oxide of H and $Al_2O_3$ is the oxide of Al. In some implementations, a PGNAA substance analyzer uses the systems and techniques described herein to measure on-line and in real time the true weight percent values of $SiO_2$, CaO, $Al_2O_3$, $Fe_2O_3$, $TiO_2$, MgO, $K_2O$, $SO_3$, Chlorine, Nitrogen, and Hydrogen.

The percentage weights of the oxides are obtained by dividing both sides of the equation by the total weight, W(total), and multiplying by 100:

$$100\% = 100\Sigma(W_{(O(i))})/W_{(total)}\%. \quad (3)$$

PGNAA most commonly uses MLR to determine the masses of the elements in the material from the measured spectrum of the material and the library of spectra of the elements in the material. It should be noted here that these measured weights are not real weights but are effective weights that are a function of the configuration of the sample being measured, i.e., the mass, neutron flux magnitude and profile, macroscopic cross section and other factors that may affect the relationship between the count rate and the elemental density. If, at this point in the analysis, the coefficients were correlated to weight percent values in the known samples, the correlation would be correct for material configurations that were the same as that used to generate that correlation but would yield errors for all other configurations.

This limitation can be eliminated by normalizing the coefficients to the sum of all of the coefficients. The coefficients times the magnitudes of their reference spectra are then equal to the relative effective mass of those elements in the known sample. Note that it is important that the units of each of the spectra should be consistent.

Since each element has a unique neutron absorption cross section, the amounts of time and the quantity of the element that are used to collect the elemental reference spectra may be different for each of the elements in order to get similar precisions for each of the elemental spectra. The magnitudes of the channels in the collected reference spectra can be multiplied times any dimensionless number without changing the precisions achieved in the data collection. If the magnitudes of the reference spectra were equal to the magnitudes of the spectra contributed by the elements to the detected spectral response of a known sample, the associated coefficient determined by MLR would be 1. There may be advantage to keeping the amplitudes of the reference spectra close to the amplitudes they contribute to the detected spectral response.

In any case, the effective weight values (which can be simply the coefficients, and whether elemental weights, molecular weights, or other) are summed 225 together to form a total effective weight for the substance being analyzed. For example, the elemental effective weight values determined for the current known sample (e.g., the MLR output coefficients) can be added together to determine an effective mass of the substance being analyzed. Obtaining the effective mass of the substance in this way ensures that the conditions (the material configurations) that affect the relationship between the elemental count rates and the weight-percent values of the elements affect the total effective mass of the substance in the same way and to the same magnitude.

The effective weight values are divided 230 by the total effective weight to generate effective weight-percent values. In some implementations, this division is done for all of the effective weight values. In some implementations, this division is done for only a subset of all of the effective weight values, where the subset is selected based on the desired output for a particular PGNAA analysis. In either case, the effective weight of an element or molecule is divided by the total effective weight of the substance being analyzed (determined from all the effective weight values for the substance) to obtain an effective weight percent of the element or compound. Note that this calculation will hold up over a broad range of sample conditions and eliminates most of the deficiencies of prior art systems, as shown by the theoretical analysis above and empirical testing.

At 235, a check is made to determine whether additional known samples remain to be processed to generate the calibration data. If so, a next known sample is placed in the PGNAA analyzer, and the detection and analysis process described above repeats. Once all the regression algorithm coefficient data has been collected and normalized (by dividing each effective weight value by the total effective weight value) to determine effective weight percent values for each of the known samples, the final calibration data can be generated for the PGNAA analyzer.

The determined effective weight percent values are correlated 240 with previously obtained weight percent values for the known samples. Note that these previously obtained weight percent values are the previously loaded, precise values, e.g., loaded at 200, and these weight percent values are weight percent values of elementals, molecules (e.g., oxides), or both. Mathematical statistical techniques are used to compare the two sets of data, and the results of the correlation 240 are calibration values that convert effective weight percent values obtained at 230 to elemental or molecular weight percent values of the know samples. This determined calibration data is then stored 245 for use during normal operation of the PGNAA analyzer.

As noted above, the effective weight percent values obtained at 230 and/or the independently obtained weight percent values for the known samples can be elemental weight percent values or molecular weight percent values. Thus, implementations include: (1) correlating detected, effective elemental weight percent values with known elemental weight percent values for the samples, (2) correlating detected, effective molecular weight percent values with known molecular weight percent values for the samples, or (3) correlating detected, effective elemental weight percent values with known molecular weight-percent values for the samples (e.g., weight percent of oxides). Thus, the calibration data can include a conversion of elemental weight percent to oxide weight percent in the known materials, i.e., the calibration data can include the relationship of the ratio of the molecular weights of the oxides to the atomic weights of the elements described above.

In any case, a mathematical statistical program can be used to determine the relationship between the determined effective weight percent values and the weight-percent values of the associated elements or molecules in the known samples. For example, matrix math can be used to determine a gain and offset for each MLR coefficient that will make the calculated weight-percent values match the known precise values of weight percent. This approach can both compensate for mass differences between elements and molecules and any measurement imperfections. Further, the result of the correlation is the determined relationship (e.g., the set of gain values and offset values) that serves to calibrate the PGNAA substance analyzer for use in processing unknown samples.

Thus, the results of the correlation between the measured effective weight percent values for the known samples and the previously obtained precise weight-percent values for the known samples is saved 245, e.g., as output to the data repository 126. The PGNAA analyzer, thus calibrated, can be used to analyze material on a belt, in a pipe, or other conveyance mechanism, with immunity from effects of belt load variation, neutron source intensity changes, moisture content, and macroscopic cross section changes in the sampled substance. All of these corrections are achieved by determining the effective mass of the sample in the manner described and dividing the effective weights of the elements or compounds by that effective mass of the sample. Every influence that changes the magnitude of counts of the elements or compounds in the sample also changes the effective mass of the sample in the same manner. Thus the quotients are true weight-percent values and are immune to influences that cause errors in prior art methods of calibration because those influences cancel in the division step. The calibration data are valid for reference spectra of the magnitude used in the calibration.

Figure 2B:
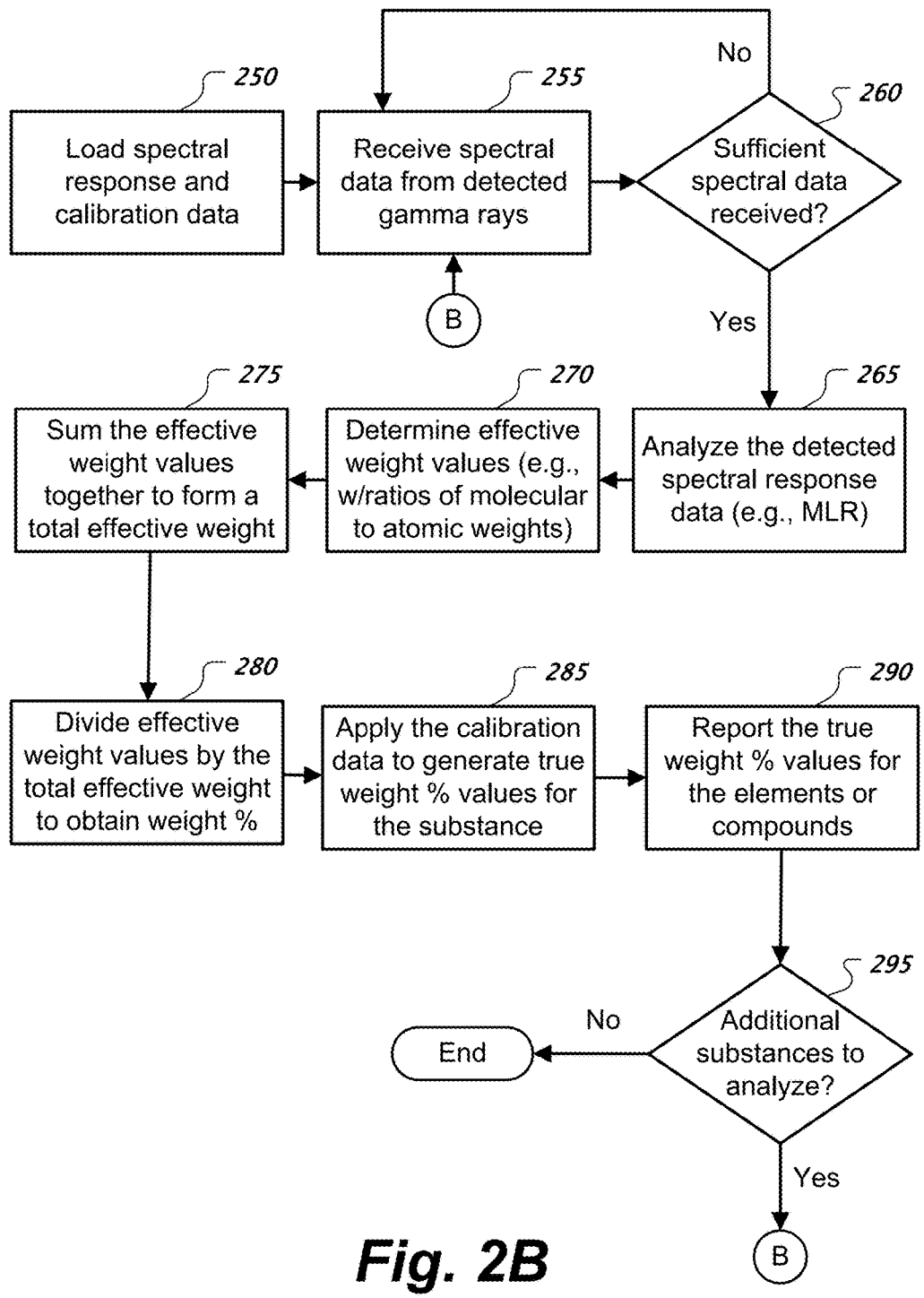
FIG. 2B shows an example of a process of generating true weight percent values using spectral data of gamma rays detected by a PGNAA substance analyzer.

FIG. 2B shows an example of a process of generating true weight percent values using spectral data of gamma rays detected by a PGNAA substance analyzer. Spectral response data for known atomic elements are loaded 250, e.g., loaded by computer 120 from data repository 126. These spectral responses are the same data used during the calibration of the PGNAA substance analyzer. Thus, the data is obtained from observations of gamma rays emitted by individual atomic elements, e.g., under laboratory conditions, and saved in the data repository 126. These spectra can be similar to (or be) what is found in text books, but are typically determined by independent analysis using a specific detector since the spectra can be unique to the detector being used. In some implementations, the entire spectrum of gamma rays of an element that is emitted promptly when that element absorbs a neutron can be used. In other implementations, only a portion of the entire spectrum is used. Moreover, in some implementations, the spectral responses for the known atomic elements are provided in the data repository in units of counts per minute per gram to facilitate processing of the data.

In addition, calibration data for the PGNAA substance analyzer is loaded 250, e.g., loaded by computer 120 from data repository 126. The calibration data was generated previously using the known samples, which were also processed by the PGNAA substance analyzer, as described above. In some implementations, the calibration data includes a gain value and an offset value for each MLR element coefficient to be generated.

Once the calibration data is loaded, the PGNAA substance analyzer is ready to process newly received spectral data from an unknown substance 104. The PGNAA substance analyzer receives 255 spectral data from an unknown substance 104. In some implementations, the process waits 255 for spectral data from detected gamma rays, and continuously, regularly or upon user input, checks 260 whether sufficient detected spectral data has been received. In some implementations, the process waits 255 for a predefined period of time (e.g. one minute) and/or until a sufficient number of counts are received before determining 260 that enough spectral data is available for further processing. For example, in some implementations, counts data is collected every five seconds, and the five second count data can be accumulated over a longer period of time, e.g., one minute, to create a data set that is ready to analyze.

Once sufficient spectral data for an unknown substance 104 has been received, the detected spectral response data is analyzed 265. This can involve performing a regression algorithm on the detected spectral data using the loaded spectral responses for known atomic elements to determine coefficients of spectrum for atomic elements detected in the spectral data, such as described above with respect to processing data from a known sample (e.g., MLR with or without background subtraction). Other regression algorithms that can be used in various implementations include logistic regression, polynomial regression, stepwise regression, ridge regression, Lasso regression, and elastic net regression. In any case, the result of this processing is a coefficient for each atomic element detected in the unknown substance 104.

Effective weight values are determined 270 based on the calculated coefficients. As with the processing of the known samples, in some implementations, the determined coefficients of spectrum are themselves used as the effective weights. Note that these are "effective" weights because they correlate with the real weights but are not the real weights themselves. In other implementations, the effective weights are generated using the calculated coefficients of spectrum as input, as described above.

For example, the effective weight values can be generated in accordance with a determined relationship between magnitudes of elemental coefficients and weight values of elements or molecules expected to be found in the unknown substance 104. In the case of elemental weight values, the determined relationship accounts for known isotopic variation in the elements typically found at a given location (e.g., based on samples from a site for which the PGNAA analysis will be performed). In the case of molecular weight values, the determined relationship accounts for the additional weight provided by known molecular compounds typically found at a given location. If the weight of an element is determined, it can be correlated to the mass of an oxide or other molecule by multiplying times the ratio of the molecular weight of that molecule to the atomic weight of that element, as described in detail above.

The effective weight values are summed 275 together to form a total effective weight for the substance being analyzed. For example, the elemental effective weight values determined based on the unknown substance 104 can be added together to determine an effective mass of the substance being analyzed. Obtaining the effective mass of the substance in this way ensures that the conditions that affect the relationship between the elemental count rates and the weight percent of the elements affect the total effective mass of the substance in the same way and to the same magnitude.

The effective weight values are divided 280 by the total effective weight to generate effective weight-percent values. In some implementations, this division is done for all of the effective weight values. In some implementations, this division is done for only a subset of all of the effective weight values, where the subset is selected based on the desired output for a particular PGNAA analysis. In either case, the effective weight of an element or molecule is divided by the total effective weight of the substance being analyzed (determined from all the effective weight values for the substance) to obtain an effective weight percent of the element or compound. Note that this calculation will hold up over a broad range of sample conditions and eliminates most of the deficiencies of prior art systems, as shown by the theoretical analysis above and empirical testing.

As noted above, in some implementations, the effective weight values of molecules are generated 270 from the coefficients of spectrum in accordance with a determined relationship between magnitudes of elemental coefficients and weight values of molecules expected to be found in the sample (e.g., correlated to the masses of the oxides). Carbonates and oxides include significant mass that typically is not included in the elemental results of PGNAA, and so these can be accounted for by determining the relationships between the elements and their respective compounds before determining the effective weight percent values of the compounds in the sample and thereby accounting for the total effective mass of the sample, which is used as the denominator in calculating the true weight percent of each compound.

In other implementations, the elemental coefficients can be used directly at 275 and 280, even when the generated weight percent values are then correlated with molecular weight percent values for the known samples. In any case, the approach used when generating the calibration data for the PGNAA substance analyzer should be the same approach used when processing new data for an unknown substance 104 using that calibration data.

Once the fully processed effective weight percent values are available for the unknown substance 104, the calibration data is applied 285 to these values to generate true weight percent values for the unknown substance 104. For example, the effective weight-percent values of elements determined for the unknown substance 104 can be converted to true weight-percent values (elemental or molecular) for the unknown substance 104 using the gains and offsets determined during the calibration for each element. As another example, the effective weight-percent values of oxides determined for the unknown substance 104 can be converted to true weight-percent values for the unknown substance 104 using the gains and offsets determined during the calibration for each element that contributes weight to an oxide.

In a sense, the summation 275 and division 280 serve to normalize the data generated from detected gamma rays, thus causing the PGNAA substance analyzer to effectively recalibrate itself automatically for each new unknown sample due to the manner in which weight-percent values are calculated. Thus, determining the total effective mass of the sample on the same basis as is the basis of determining the effective mass of each compound enables accurately determining the true weight percent of each of those compounds. The basis that is the same for the total sample and for each element includes the same macroscopic cross section, the same sample depth, the same sample density, the same sample moisture content, the same neutron flux level and contour, etc. Because the basis is identical in the determining of each effective mass, these influences cancel out in the determination of the weight-percent values, and the weight-percent values obtained in this way are, indeed, the true weight-percent values.

This is in contrast to prior art systems, which determine the weight-percent values by measuring the sample mass directly or by implied measurement of the sample mass under certain fixed conditions, which results in errors when any of these influences change. Thus those systems should be calibrated again for major changes in sample thickness, material type, neutron source strength, moisture content, density, macroscopic cross section, etc. Minor changes in these influences also affect the measurements and cause the accuracy of measurement to become poorer.

The determined true weight-percent values (elements or compounds) for the unknown substance 104 are reported 290. This can involve displaying weight-percent data on a computer screen, transmitting weight-percent data to a process control system, storing the weight-percent data in a data repository, or other, or all. Further, a check can be made 295 as to whether additional substances are to be analyzed. If so, the process repeats. In some implementations, the process of FIG. 2B is ongoing and doesn't stop until terminated by a user. For example, the process of FIG. 2B can be performed using a PGNAA analyzer that actively processes gamma ray detection data from a stream of material, e.g., on a conveyor belt or in a slurry pipe.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented using one or more modules of computer program instructions encoded on a computer-readable medium for execution by, or to control the operation of, data processing apparatus. The computer-readable medium can be a manufactured product, such as hard drive in a computer system or an optical disc sold through retail channels, or an embedded system with built-in memory. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results.

What is claimed is:

1. A PGNAA (Prompt-Gamma, Neutron-Activation Analysis) substance analyzer comprising:
   a source of neutrons;
   an opening arranged with respect to the source of neutrons to receive a substance;
   a gamma ray detector arranged with respect to the opening to detect gamma rays emanating at least from the substance in response to absorption of neutrons by the substance; and
   one or more computational devices configured to
      receive spectral data of the detected gamma rays,
      perform a regression algorithm on the spectral data using a data repository of spectral responses for known atomic elements to determine coefficients of spectrum for atomic elements detected in the spectral data,
      sum effective weight values, corresponding to the coefficients of spectrum, together to form a total effective weight value for the substance being analyzed,
      divide each of two or more of the effective weight values by the total effective weight value for the substance being analyzed to generate effective weight-percent values corresponding to two or more respective ones of the atomic elements detected in the spectral data, and
      generate final weight-percent values from the effective weight-percent values, for the substance being analyzed, based on a correlation of (a) previous effective weight-percent values obtained for known samples with (b) elemental or molecular weight-percent values obtained for the known samples.

2. The PGNAA substance analyzer of claim 1, wherein the effective weight values are the coefficients of spectrum determined by the regression algorithm.

3. The PGNAA substance analyzer of claim 2, wherein the final weight-percent values are molecular weight-percent values for the substance being analyzed.

4. The PGNAA substance analyzer of claim 2, wherein the regression algorithm comprises MLR (multiple linear regression).

5. The PGNAA substance analyzer of claim 4, wherein the spectral responses for the known atomic elements are provided in the data repository in units of counts per minute per gram.

6. The PGNAA substance analyzer of claim 1, wherein the one or more computational devices are configured to generate the effective weight values in accordance with a determined relationship between magnitudes of elemental coefficients and weight values of elements or molecules.

7. The PGNAA substance analyzer of claim 6, wherein the one or more computational devices are configured to generate the effective weight values by multiplying the coefficients of spectrum by respective ratios of molecular weight to atomic weight for detected elements.

8. The PGNAA substance analyzer of claim 1, wherein the source of neutrons is an isotopic radioactive source, and the PGNAA substance analyzer comprises:
   a neutron moderating material arranged with respect to the isotopic radioactive source to slow velocities of neutrons from the isotopic radioactive source; and
   a radiation shielding material arranged with respect to the opening and the gamma ray detector to reduce an amount of radiation escaping the substance analyzer.

9. The PGNAA substance analyzer of claim 1, wherein the source of neutrons is an electrically powered neutron generator.

10. The PGNAA substance analyzer of claim 1, wherein the one or more computational devices are configured to:
   receive calibration spectral data of gamma rays detected from the known samples;
   perform the regression algorithm on the calibration spectral data using the data repository of spectral responses for known atomic elements to determine calibration coefficients of spectrum for atomic elements detected in the calibration spectral data;
   sum calibration effective weight values, corresponding to the calibration coefficients of spectrum, together to form a total calibration effective weight value for each of the known samples;
   divide each of two or more of the calibration effective weight values by the total calibration effective weight value for each respective known sample to generate the previous effective weight-percent values for the known samples; and correlate the previous effective weight-percent values with the elemental or molecular weight-percent values obtained for the known samples to generate calibration data;

wherein generating the final weight-percent values comprises applying the calibration data to the effective weight-percent values for the substance being analyzed.

11. A PGNAA (Prompt-Gamma, Neutron-Activation Analysis) substance analyzer comprising:

an isotopic radioactive source of neutrons;

a neutron moderating material arranged with respect to the isotopic radioactive source to slow velocities of neutrons from the isotopic radioactive source;

an opening arranged with respect to the source of neutrons to receive a substance;

a gamma ray detector arranged with respect to the opening to detect gamma rays emanating at least from the substance in response to absorption of neutrons by the substance; and one or more computational devices configured to receive spectral data of the detected gamma rays, perform a regression algorithm on the spectral data using a data repository of spectral responses for known atomic elements to determine coefficients of spectrum for atomic elements detected in the spectral data, use the coefficients of spectrum directly as effective weight values of the atomic elements detected in the spectral data, sum the effective weight values together to form a total effective weight value for the substance being analyzed, divide each of two or more of the effective weight values by the total effective weight value for the substance being analyzed to generate effective weight-percent values for the atomic elements detected in the spectral data, and generate molecular weight-percent values from the effective weight-percent values, for the substance being analyzed, based on a correlation of (a) previous effective weight-percent values obtained for known samples with (b) molecular weight-percent values obtained for the known samples.

12. The PGNAA substance analyzer of claim 11, wherein the regression algorithm comprises MLR (multiple linear regression).

13. The PGNAA substance analyzer of claim 12, wherein the spectral responses for the known atomic elements are provided in the data repository in units of counts per minute per gram.

14. The PGNAA substance analyzer of claim 11, wherein the one or more computational devices are configured to:

receive calibration spectral data of gamma rays detected from the known samples;

perform the regression algorithm on the calibration spectral data using the data repository of spectral responses for known atomic elements to determine calibration coefficients of spectrum for atomic elements detected in the calibration spectral data;

use the calibration coefficients of spectrum directly as calibration effective weight values of the atomic elements detected in the spectral data, sum the calibration effective weight values together to form a total calibration effective weight value for each of the known samples;

divide each of two or more of the calibration effective weight values by the total calibration effective weight value for each respective known sample to generate the previous effective weight-percent values for the known samples; and correlate the previous effective weight-percent values with the molecular weight-percent values obtained for the known samples to generate calibration data;

wherein generating the molecular weight-percent values comprises applying the calibration data to the effective weight-percent values for the substance being analyzed.

15. A non-transitory machine readable medium encoding instructions operable to receive PGNAA (Prompt-Gamma, Neutron-Activation Analysis) spectral data and to cause a computer to perform operations comprising:

running a regression algorithm on the PGNAA spectral data using a data repository of spectral responses for known atomic elements to determine coefficients of spectrum for atomic elements detected in the PGNAA spectral data;

summing effective weight values, corresponding to the coefficients of spectrum, together to form a total effective weight value for the substance being analyzed;

dividing each of two or more of the effective weight values by the total effective weight value for the substance being analyzed to generate effective weight-percent values corresponding to two or more respective ones of the atomic elements detected in the PGNAA spectral data; and generating final weight-percent values from the effective weight-percent values, for the substance being analyzed, in accordance with calibration data generated by correlating effective weight-percent values obtained for known samples with elemental or molecular weight-percent values obtained previously for the known samples.

16. The non-transitory machine readable medium of claim 15, wherein running the regression algorithm on the PGNAA spectral data comprises performing MLR (multiple linear regression) processing of the PGNAA spectral data.

17. The non-transitory machine readable medium of claim 15, wherein the effective weight values are the coefficients of spectrum determined by the regression algorithm.

18. The non-transitory machine readable medium of claim 17, wherein the spectral responses for the known atomic elements are provided in the data repository in units of counts per minute per gram.

19. The non-transitory machine readable medium of claim 15, wherein the operations comprise generating the effective weight values in accordance with a determined relationship between magnitudes of elemental coefficients and weight values of elements or molecules.

20. The non-transitory machine readable medium of claim 19, wherein generating the effective weight values comprises multiplying the coefficients of spectrum by respective ratios of molecular weight to atomic weight for detected elements.

21. The non-transitory machine readable medium of claim 19, wherein the operations comprise:

receiving calibration spectral data of gamma rays detected from the known samples;

running the regression algorithm on the calibration spectral data using the data repository of spectral responses for known atomic elements to determine calibration coefficients of spectrum for atomic elements detected in the calibration spectral data;

summing calibration effective weight values, corresponding to the calibration coefficients of spectrum, together to form a total calibration effective weight value for each of the known samples;

dividing each of two or more of the calibration effective weight values by the total calibration effective weight value for each respective known sample to generate the effective weight-percent values obtained for the known samples; and correlating the effective weight-percent values obtained for the known samples with the elemental or molecular weight-percent values obtained for the known samples to generate the calibration data.

22. A non-transitory machine readable medium encoding instructions operable to receive PGNAA (Prompt-Gamma, Neutron-Activation Analysis) spectral data and to cause a computer to perform operations comprising:

running a regression algorithm on the PGNAA spectral data using a data repository of spectral responses for known atomic elements to determine coefficients of spectrum for atomic elements detected in the PGNAA spectral data;

summing the coefficients of spectrum together to form a total effective weight value for the substance being analyzed;

dividing each of two or more of the coefficients of spectrum by the total effective weight value for the substance being analyzed to generate effective weight-percent values for the atomic elements detected in the PGNAA spectral data; and generating molecular weight-percent values from the effective weight-percent values, for the substance being analyzed, in accordance with calibration data generated by correlating effective weight-percent values obtained for known samples with molecular weight-percent values obtained previously for the known samples.

23. The non-transitory machine readable medium of claim 22, wherein running the regression algorithm on the PGNAA spectral data comprises performing MLR (multiple linear regression) processing of the PGNAA spectral data.

24. The non-transitory machine readable medium of claim 22, wherein the spectral responses for the known atomic elements are provided in the data repository in units of counts per minute per gram.

25. The non-transitory machine readable medium of claim 22, comprising:

receiving calibration spectral data of gamma rays detected from the known samples;

running the regression algorithm on the calibration spectral data using the data repository of spectral responses for known atomic elements to determine calibration coefficients of spectrum for atomic elements detected in the calibration spectral data;

summing the calibration coefficients of spectrum together to form a total calibration effective weight value for each of the known samples;

dividing each of two or more of the calibration coefficients of spectrum by the total calibration effective weight value for each respective known sample to generate the effective weight-percent values obtained for the known samples; and correlating the effective weight-percent values obtained for the known samples with the molecular weight-percent values obtained for the known samples to generate the calibration data.

\* \* \* \* \*